United States Patent
Rheude et al.

(10) Patent No.: US 6,288,282 B1
(45) Date of Patent: *Sep. 11, 2001

(54) PROCESS FOR PREPARING IONONES

(75) Inventors: Udo Rheude, Otterstadt; Ulrich Hörcher, Mannheim; Dietmar Weller, Ludwigshafen; Manfred Stroezel, Ilvesheim, all of (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/567,268

(22) Filed: May 9, 2000

Related U.S. Application Data

(63) Continuation of application No. 09/147,262, filed as application No. PCT/EP97/02249 on May 2, 1997.

(30) Foreign Application Priority Data

May 14, 1996 (DE) .............................................. 196 19 557

(51) Int. Cl.[7] .................................................... C07C 49/21
(52) U.S. Cl. ........................................... 568/343; 568/349
(58) Field of Search ..................................... 568/343, 349

(56) References Cited

U.S. PATENT DOCUMENTS 4,565,894 * 1/1986 Hertel et al. ......................... 568/349

FOREIGN PATENT DOCUMENTS

4220239 * 12/1993 (DE) .

* cited by examiner

Primary Examiner—Sreeni Padmanabhan
(74) Attorney, Agent, or Firm—Oblon, Spivak, McClelland, Maier & Neustadt, P.C.

(57) ABSTRACT

Process for the continuous preparation of α- and/or β-ionone or homologous compounds using concentrated sulfuric acid at temperatures from 20 to 90° C., in the presence of organic solvents or diluents with cooling and by subsequent termination of the reaction by hydrolysis of the reaction mixture with water or dilute sulfuric acid, wherein both the cyclization of pseudoionones and the subsequent hydrolysis of the reaction mixture are carried out in a virtually adiabatic reaction in one or more reaction mixing pump(s) which are connected in series and each of which consists essentially of a rotationally symmetrical mixing chamber formed from a peripheral wall and two end walls and of a mixing rotor made of material inert to sulfuric acid and with rotational drive, where the mixing chamber has at least one inlet opening for each component and one outlet opening for the reaction mixture, and annular channels in fluid connection to one another in the end walls, and wherein the heat of the two reactions is in each case partly or wholly removed with the aid of a downstream heat exchanger.

10 Claims, 1 Drawing Sheet

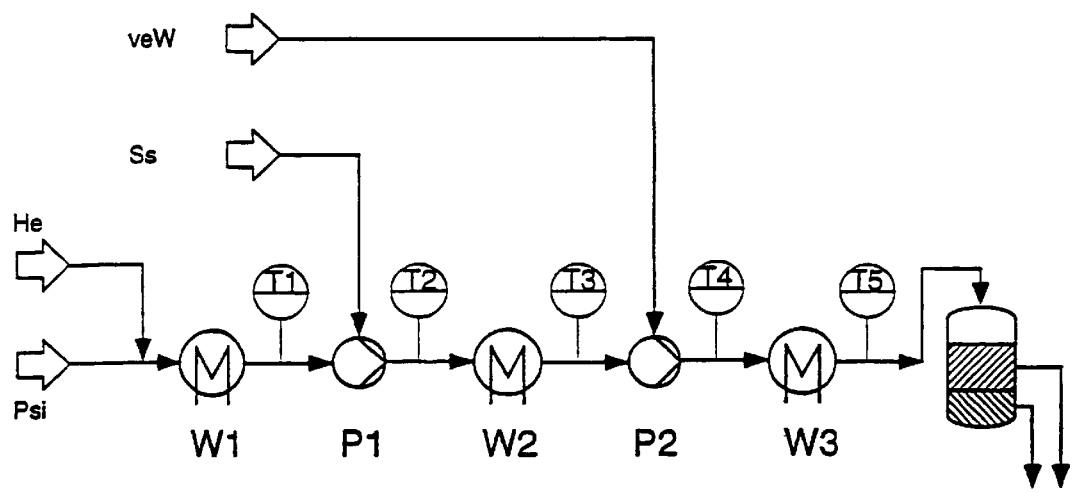

PROCESS FOR PREPARING IONONES

This application is a CON of Ser. No. 09/147262 filed as application No. PCT/EP97/02249 on May 2, 1997 now U.S. Pat. No. 6,140,542.

BACKGROUND OF THE INVENTION

1. Field of the Invention

The invention relates to an improved process for the continuous preparation of α- and/or β-ionone or homologs of these compounds by cyclizing pseudoionones using concentrated sulfuric acid in the presence of organic solvents or diluents and by diluting the reaction mixture with water.

2. Description of the Background

It is known that a mixture of α- and β-ionones is obtained on cyclization of pseudoionone in the presence of acids such as sulfuric acid or phosphoric acid. The ratio of the amounts in which these compounds are produced depends greatly on the conditions under which the reaction takes place.

Since both α-ionone and β-ionone are of great industrial importance, there has been no lack of attempts to develop a maximally advantageous process for their preparation.

Processes for cyclizing pseudoionone with concentrated sulfuric acid have proven particularly suitable. Since this reaction is highly exothermic, it is very important to remove the heat produced in the reaction as quickly as possible in order to avoid local overheating. For this purpose, in the known processes, diluents have been added to the reaction mixture. Thus, for example, DE Patents 10 80 105 and 16 68 505 disclose the use of aliphatic or cycloaliphatic hydrocarbons. The disadvantage of this process is that resins are relatively quickly deposited in the reaction vessels in the procedure described therein, and interfere with continuous operation.

According to IN patent 77 225, the reaction is carried out in the presence of aliphatic chlorinated hydrocarbons such as methylene chloride, ethylene dichloride, chloroform and tetrachloromethane at temperatures from −10° C. to +10° C. According to the description in DE-A 15 68 108, this Indian process is disadvantageous because the aliphatic chlorinated hydrocarbons eliminate hydrogen chloride with sulfuric acid, leading within a short time to corrosion of the apparatus used. To avoid these disadvantages, it is recommended to carry out the cyclization at −25° C. to +10° C. in a mixture of low-boiling hydrocarbons and chlorinated hydrocarbons. The disadvantage of the two last-mentioned processes is that the reaction temperature must be kept low with costly coolants in order to obtain good ionone yields.

Further known processes entail removing the considerable heat of cyclization by evaporative cooling with liquid gases. Thus, liquid sulfur dioxyde [sic] is used in the process of DE patent 16 68 496, propane, butane or isobutane is used in the process of DE patent 16 68 505, and methyl chloride is used in the process of DE patent 19 17 132, at temperatures from −25° C. to room temperature, preferably temperatures below +10° C.

The results obtained in these processes are generally quite good. The disadvantage thereof is the large expenditure necessary for reliquefying the gas vaporized in the reaction.

Further processes for preparing β-ionone are disclosed in CS patent 179 046, SU patent 458 540 and SU patent 547 445, wherein thorough mixing of the reactants and rapid removal of heat are achieved by using a thin film reactor. The disadvantage of the two last-mentioned processes is that only about 3 to 6 kg of β-ionone are obtained per m² of thin film area and hour, and thus transfer to the industrial scale would result in enormous apparatus. The disadvantage of the process in the Czech patent is that temperatures between 10 and 15° C. must be used to obtain good yields, which makes costly coolants necessary once again.

In all the known processes there is always formation of a mixture of α- and β-ionones. According to DE patents 10 80 105, 16 68 496 and 16 68 505, β-ionone is preferentially obtained at reaction temperatures from −20 to 0° C., while the α-ionone content increases at temperatures from −10 to 25° C.

In addition, EP 133 668 discloses a process for the continuous preparation of ionones, in which the pseudoionone is mixed with concentrated sulfuric acid, in a hydrocarbon which boils at 25 to 65° C. under the reaction conditions, with vigorous mixing and evaporative cooling by partial or complete vaporization of the solvent, in such a way that the temperature of the reaction mixture is between 25 and 65° C., and the residence time until the reaction mixture is diluted with water is 0.05 to 20 seconds. The disadvantage of this process, which functions very well in small systems, is that difficulties arise on transfer to the industrial scale.

Finally, EP 628 544 A1 discloses a process for preparing β-ionone by sulfuric acid-catalyzed cyclization of pseudoionone in a two-phase solvent system consisting of concentrated sulfuric acid and a second solvent which is essentially immiscible with water, where liquid carbon dioxide under pressure is used as second solvent. The disadvantages of this process are that very high pressures and rather low temperatures must be used, and that the complexity of the apparatus for carrying out the process is considerable.

β-Ionone is an essential precursor for the industrial preparation of vitamin A. In this case, a high content of α-ionone reduces the yield. Pure α-ionone and alkyl-substituted ionones are, on the other hand, in demand as fragrances in which a high content of β-ionone would have an interfering effect.

SUMMARY OF THE INVENTION

It is an object of the present invention to develop a process with which it is possible to prepare both α-ionone of maximal purity and β-ionone of maximal purity or else alkyl-substituted ionones on the industrial scale in a maximally advantageous manner in high yields and space-time yields.

BRIEF DESCRIPTION OF THE DRAWINGS

The drawing illustrates a system utilized with the present process.

DETAILED DESCRIPTION OF THE PREFERRED EMBODIMENTS

We have found that this object is achieved by a process for preparing ionones of the general formulae I and II

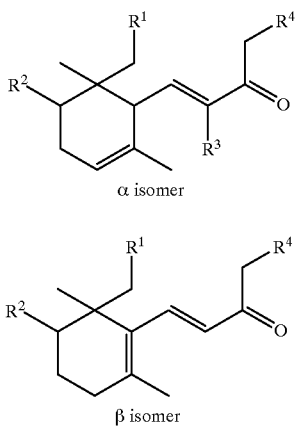

α isomer

β isomer in which $R^1$ to $R^4$ are H, —$CH_3$ or —$C_2H_5$, by cyclizing pseudoionones of the general formula III

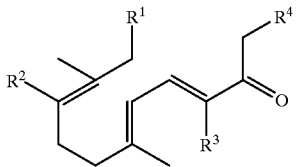

using concentrated sulfuric acid at temperatures from 20 to 90° C., preferably 35 to 65° C., in particular 40 to 60° C., in the presence of organic solvents or diluents with cooling and by subsequent termination of the reaction by hydrolysis of the reaction mixture with water or dilute sulfuric acid, wherein both the cyclization of pseudoionones of the formula III and the subsequent hydrolysis of the reaction mixture are carried out in a virtually adiabatic reaction in one or more reaction mixing pump(s) which are connected in series and each of which consists essentially of a rotationally symmetrical mixing chamber formed from a peripheral wall and two end walls and of a mixing rotor made of material inert to sulfuric acid and with rotational drive, where the mixing chamber has at least one inlet opening for each component and one outlet opening for the reaction mixture, and annular channels in fluid connection to one another in the end walls, and wherein the heat of the two reactions is in each case partly or wholly removed with the aid of a downstream heat exchanger.

A pump mixing apparatus suitable as so-called reaction mixing pump for the novel process is described, for example, in DE-A-42 20 239 which is incorporated in these applications by reference. Various designs of such reaction mixing pumps are commercially available, for example from K-ENGINEERING, Sessinghausen 26, 58 566 Kierspe, Germany. These apparatuses combine the properties of a pump, of a mixer for particularly efficient mixing, and of the reactor both for the cyclization of pseudoionones of the formula III and for the subsequent hydrolysis of the reaction mixture. This results in the elaboration of the apparatus required for the novel process being very low.

The mixing chamber of this reaction pump consists of a bearing flange and of a cylindrical insert element with a peripheral wall overlapping the mixing rotor. In the peripheral wall of reaction pump(s) 1 there is an inlet opening each for the pseudoionone solution and the concentrated sulfuric acid, and an outlet opening for the reaction mixture, and in that of the reaction pump(s) 2 there is an inlet opening each for the reaction mixture and water or dilute sulfuric acid, and an outlet opening for the reaction mixture which, after cooling in the downstream heat exchanger, can in a manner known per se be separated into the two phases and the organic phase can be worked up by distillation.

It has proven particularly beneficial to design the inlet openings of the reaction pumps to taper like a nozzle in the direction of the reaction mixing chamber(s) because this results in a type of suction effect.

It is, of course, necessary for the parts of the reaction pump which come into contact with the reaction mixture to be made of material which is stable to sulfuric acid, or to be covered therewith. Material which is stable to sulfuric acid and which may be mentioned are metals or metal alloys, such as Hastelloy, titanium or nickel; plastics such as polyethylene (PE), polypropylene (PP), polyvinylidene fluoride (PVDF) or polytetrafluoroethylene (PFE [sic]), or oxide ceramics.

The technical design of the reaction pumps normally accords with the required pressure conditions in the mixing chamber.

In general, both the cyclization of pseudoionones of the formula III and the subsequent hydrolysis of the reaction mixture are carried out under pressures of from 1 to 10 bar, preferably 1.5 to 2.5 bar.

The residence times of the reaction mixtures in the reaction pumps are determined by the feed rates set and the technical design of the reaction pumps, or by the speed of rotation of the mixing rotor.

To prepare α- or β-ionone by cyclization of pseudoionone, both the cyclization and the subsequent hydrolysis of the reaction mixture are carried out with residence times of from 0.1 to 10 seconds, preferably 0.5 to 2 seconds.

The cyclization of homologs of pseudoionone, that is to say ionones of the formula III in which at least one of the radicals $R^1$ to $R^4$ are [sic] —$CH_3$ or —$C_2H_5$, does in fact require longer residence times. It may therefore be advantageous, especially in the preparation of homologs of α- or β-ionone, to use two or more reaction pumps connected in series for each reaction step, in each case in place of one reaction pump.

The residence times for the preparation of methylionones, for example, are about 0.2 to 20 seconds, in particular 1 to 4 seconds, depending on the reaction temperature.

The pseudoionones used as starting compounds are known compounds which can be obtained in a known manner.

The concentration of the sulfuric acid used in the cyclization can be between 60 and 100% by weight. The strength of the sulfuric acid used is preferably from 80 to 98% by weight, in particular 90 to 96% by weight. In general, 2 to 10 mol, preferably 2 to 7 mol, in particular 4–6 mol, of sulfuric acid are used per mole of pseudoionone. Mainly α-ionone is obtained on use of 2 to 3 mol of sulfuric acid per mole of pseudoionone, whereas β-ionone with a content of less than 2% of α-ionone is obtained on use of more than 5 mol of sulfuric acid per mole of pseudoionone.

Solvents which are essentially suitable are aromatic, aliphatic or cycloaliphatic hydrocarbons, and aliphatic chlorinated hydrocarbons. Mention may be particularly made of pentane, hexane, heptane, isopentane and cyclohexane or mixtures thereof. It is, of course, particularly advantageous to use solvents which boil at temperatures between 25 and 100° C. under normal conditions. Hexane (boiling point= 68.7° C.) is preferably used.

The amount of solvent can be varied within wide limits. The best results are, however, obtained when the solutions used contain the pseudoionone in a concentration of 5 to 95% by weight, preferably 10 to 50% by weight, particularly 10 to 30% by weight.

Immediately after the end of the cyclization, the reaction mixture, which generally has a temperature of 35 to 65° C., is cooled to about 20 to 60° C.—depending on the reaction temperature—in a heat exchanger and, for definitive stoppage of the reaction, diluted with water in a second reaction pump, or a series of reaction pumps. As a rule, 1.5 to 2.5 l of water are used per kg of sulfuric acid.

Immediately after leaving the hydrolysis reaction pump (s), the reaction mixture, which generally has temperatures of about 35 to 65° C., is cooled to temperatures of about 20 to 60° C., preferably 30–50° C., in another heat exchanger, and then the aqueous sulfuric acid phase is separated in a phase-separation vessel from the resulting ionone solution, and the latter is worked up by distillation in a manner known per se.

after leaving the reaction pump 1, part of the heat liberated was removed by cooling to about 40° C. (cf. T3 in Tab. 1) in the heat exchanger W2. The reaction mixture was then sucked into a second apparatus for pumping and preparing mixtures (called reaction pump P2 hereinafter) where it was mixed under pressures from 1 to 10 bar and with residence times between 0.1 and 10 seconds thoroughly with deionized water (vew). The heat produced in the hydrolysis reaction was substantially removed by cooling to about 40° C. in a downstream heat exchanger W3. The dilute sulfuric acid was separated from the resulting ionones in a downstream phase-separation vessel.

Tab. 1 indicates the amounts of α- and β-ionones (stated in percentage areas determined by gas chromatography) present in the crude discharge.

|  | Examples | | | | | | | | |
|---|---|---|---|---|---|---|---|---|---|
|  | 1 | 2 | 3 | 4 | 5 | 6 | 7 | 8 | 9 |
| Pseudoionone feed rate [kg/h] | 135 | 270 | 260 | 150 | 200 | 135 | 300 | 135 | 135 |
| Hexane feed rate [kg/h] | 800 | 800 | 800 | 800 | 800 | 800 | 800 | 800 | 800 |
| Sulfuric acid feed rate [kg/h] | 370 | 740 | 710 | 410 | 550 | 340 | 820 | 380 | 400 |
| Sulfuric acid content [% by wt] | 93 | 93 | 95 | 95 | 95 | 98 | 95 | 91 | 84 |
| Hydrolysis water feed rate [kg/h] | 765 | 1500 | 1130 | 700 | 1000 | 765 | 1050 | 820 | 820 |
| Beta-ionone content in crude discharge [GC % area] | 90.7 | 93.0 | 93.4 | 93.5 | 91.8 | 92.2 | 93.5 | 87.3 | 57.3 |
| Alpha-ionone content in crude discharge [GC % area] | 3.0 | 1.9 | 1.2 | 1.4 | 1.5 | 0.6 | 1.2 | 5.2 | 36.1 |
| Beta-ionone yield [%] | 81.0 | 82.0 | 85.5 | 84.7 | 81.9 | 77.5 | 82.6 | 79.5 | n.d. |
| Temperature T1 [° C.] | 10 | −2 | −3 | 12 | 5 | 5 | −7 | 10 | 10 |
| Temperature T2 [° C.] | 47 | 54 | 59 | 50 | 59 | 52 | 59 | 49 | 42 |
| Temperature T3 [° C.] | 40 | 40 | 41 | 40 | 41 | 39 | 44 | 46 | 40 |
| Temperature T4 [° C.] | 52 | 52 | 61 | 57 | 58 | 58 | 64 | 47 | 42 |
| Temperature T5 [° C.] | 40 | 40 | 40 | 40 | 40 | 40 | 40 | 40 | 40 |

It is possible with the aid of the novel process to prepare α- and β-ionones and homologs thereof in high yield and high space-time yield in an industrially very simple and advantageous manner. The novel process is outstandingly suitable both in terms of the system costs, the space required, the energy consumption, the yield and the personnel required.

The following examples are intended to illustrate the novel process.

EXAMPLES 1–9

In a system as depicted diagrammatically in the appended process scheme (cf. Figure), a mixture of, in each case, the amounts of pseudoionone (Psi) and hexane (He) evident from the following table (Tab1) was precooled in a heat exchanger W1 to the temperature T1 indicated in Tab. 1, and the cooled mixture was pumped by an apparatus for pumping and preparing mixtures (called reaction pump P1 hereinafter) under pressures between 1 and 10 bar and with residence times between 0.1 and 10 seconds at the temperatures T2 evident from Tab. 1 with concentrated sulfuric acid (Ss) of the concentration evident from Tab. 1, and vigorously mixed, and thus the pseudoionone was converted into a mixture of the ionones evident from Tab. 1. Immediately

We claim:

1. A process for the continuous preparation of ionones of the formulae I and II

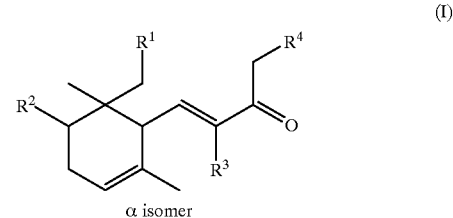

α isomer (I)

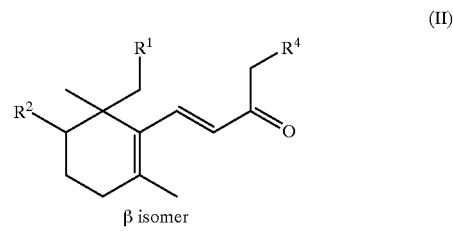

β isomer (II)

in which R¹ to R⁴ are H, —CH₃ or —C₂H₅, comprising cyclizing pseudoionones of the formula III

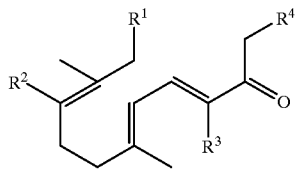
(III)

using concentrated sulfuric acid at temperatures from 20 to 90° C. in the presence of organic solvents or diluents with cooling; terminating the reaction by hydrolysis of the reaction mixture with water, wherein both the cyclization of pseudoionones of the formula III and the subsequent hydrolysis of the reaction mixture are carried out in an essentially adiabatic reaction in one or more reaction mixing pumps(s) which are connected in series and each of which comprises a rotationally symmetrical mixing chamber formed from a peripheral wall and two end walls and of a mixing rotor made of material inert to sulfuric acid and with rotational drive, where the mixing chamber has in the peripheral wall at least one inlet opening for each component and one outlet opening for the reaction mixture, and annular channels in fluid connection to one another in the end walls, and wherein the heat of the two reactions is in each case partly or wholly removed with the aid of a downstream heat exchanger.

2. The process as claimed in claim 1, wherein the cyclization of the pseudoionones and the subsequent hydrolysis of the reaction mixture is under pressures from 1 to 10 bar.

3. The process as claimed in claim 1, wherein the cyclization of pseudoionone and the subsequent hydrolysis of the reaction mixture is with residence times of from 0.1 to 10 seconds.

4. The process as claimed in claim 1, wherein the cyclization of the pseudoionones of the formula III and the hydrolysis of the reaction mixture comprises a solvent or diluent selected from the group consisting of pentane, hexane, heptane and mixtures thereof.

5. The process as claimed in claim 1, wherein both the cyclization of the pseudoionones of the formula III and the subsequent hydrolysis of the reaction mixture are carried out at temperatures from 35 to 65° C.

6. The process as claimed in claim 1, wherein the cyclization of the pseudoionones of the formula III comprises 60 to 100% sulfuric acid by weight.

7. The process as claimed in claim 1, wherein the pseudoionones are in a solvent or diluent solution at a concentration of 5 to 95% by weight.

8. The process as claimed in claim 2, wherein the pressure is from 1.5 to 2.5 bar.

9. The process as claimed in claim 3, wherein the residence times is from 0.5 to 2 seconds.

10. The process of claim 1, wherein cyclization and subsequent hydrolysis comprises solvents or diluents selected from the group consisting of aromatic hydrocarbons, aliphatic hydrocarbons, cycloaliphatic hydrocarbons, aliphatic chlorinated hydrocarbons, and mixtures thereof.

* * * * *